United States Patent
Shimuta

(10) Patent No.: US 9,742,902 B2
(45) Date of Patent: Aug. 22, 2017

(54) MOBILE APPARATUS

(71) Applicant: MURATA MANUFACTURING CO., LTD., Nagaokakyo-Shi, Kyoto-fu (JP)

(72) Inventor: Toru Shimuta, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 14/133,149

(22) Filed: Dec. 18, 2013

(65) Prior Publication Data

US 2014/0106816 A1    Apr. 17, 2014

Related U.S. Application Data

(63) Continuation of application No. PCT/JP2012/003224, filed on May 17, 2012.

(30) Foreign Application Priority Data

Jun. 24, 2011   (JP) .................................. 2011-140571

(51) Int. Cl.
*G06F 3/02* (2006.01)
*H04M 1/725* (2006.01)
(Continued)

(52) U.S. Cl.
CPC ....... *H04M 1/72569* (2013.01); *A61B 5/6898* (2013.01); *G06F 3/04883* (2013.01);
(Continued)

(58) Field of Classification Search
CPC ...... G06F 3/041; G06F 3/0412; G06F 3/0416; G06F 2203/04106; H04M 1/72569; H04M 1/725
(Continued)

(56) References Cited

U.S. PATENT DOCUMENTS 6,790,178 B1 *   9/2004   Mault .................. A61B 5/0011
                                                                        128/903
7,900,156 B2      3/2011   Andre et al.
(Continued)

FOREIGN PATENT DOCUMENTS

CN         1310982 A        9/2001
CN         1830382 A        9/2006
(Continued)

OTHER PUBLICATIONS

Written Opinion and International Search Report issued in PCT/JP2012/003224, mailed on Jun. 26, 2012.

*Primary Examiner* — Jason Mandeville
(74) *Attorney, Agent, or Firm* — Arent Fox LLP

(57) ABSTRACT

A smart phone includes photoelectric pulse wave sensing units that obtain photoelectric pulse wave signals from hands holding the smart phone, a touch screen on which a plurality of operation switches that accept operations performed by thumbs are displayed, and a switch arrangement changing unit that changes the arrangement of the displayed plurality of operation switches. The switch arrangement changing unit, when photoelectric pulse wave signals are obtained by the photoelectric pulse wave sensing units, changes the arrangement of the operation switches displayed on the touch screen in such a manner that the operation switches are arranged along a circular arc of a virtual circle whose center is located at a carpometacarpal joint of the thumb of a right hand performing operations and whose radius is the distance from the carpometacarpal joint to the tip of the thumb.

15 Claims, 13 Drawing Sheets

(51) Int. Cl.
*A61B 5/00* (2006.01)
*G06F 3/0488* (2013.01)
*G06F 3/041* (2006.01)
*A61B 5/01* (2006.01)
*A61B 5/0205* (2006.01)
*A61B 5/0402* (2006.01)
*A61B 5/0488* (2006.01)
*A61B 5/07* (2006.01)
*A61B 5/1455* (2006.01)

(52) U.S. Cl.
CPC .............. *A61B 5/01* (2013.01); *A61B 5/0205* (2013.01); *A61B 5/0402* (2013.01); *A61B 5/0488* (2013.01); *A61B 5/07* (2013.01); *A61B 5/1455* (2013.01); *A61B 5/4266* (2013.01); *A61B 5/4872* (2013.01); *G06F 3/0412* (2013.01); *G06F 3/0416* (2013.01); *H04M 2250/22* (2013.01)

(58) Field of Classification Search
USPC .......................................... 345/169, 173–177
See application file for complete search history.

(56) References Cited

U.S. PATENT DOCUMENTS

| | | | | |
|---|---|---|---|---|
| 8,031,175 | B2* | 10/2011 | Rigazio | G06F 3/04883 345/158 |
| 8,106,783 | B2* | 1/2012 | Wada | A61B 5/02416 340/426.11 |
| 8,109,874 | B2 | 2/2012 | Kong et al. | |
| 8,206,309 | B2* | 6/2012 | Oh | A61B 5/021 600/324 |
| 8,368,658 | B2* | 2/2013 | Brisebois | G06F 3/03547 345/156 |
| 8,384,683 | B2* | 2/2013 | Luo | G06F 1/1626 345/158 |
| 8,493,342 | B2* | 7/2013 | Park | G06F 1/1626 345/173 |
| 8,508,475 | B2* | 8/2013 | Gear | G06F 1/1626 345/157 |
| 8,514,186 | B2* | 8/2013 | Tan | G06F 3/04883 178/18.01 |
| 8,526,998 | B2* | 9/2013 | Koide | A61B 5/02438 455/550.1 |
| 2001/0034491 | A1 | 10/2001 | Benson et al. | |
| 2006/0085757 | A1 | 4/2006 | Andre et al. | |
| 2006/0197750 | A1* | 9/2006 | Kerr | G06F 1/1626 345/173 |
| 2006/0238517 | A1* | 10/2006 | King | G06F 1/1626 345/173 |
| 2007/0060807 | A1 | 3/2007 | Oishi | |
| 2007/0299322 | A1* | 12/2007 | Miyajima | A61B 5/0008 600/301 |
| 2008/0249382 | A1* | 10/2008 | Oh | A61B 5/021 600/324 |
| 2008/0306395 | A1 | 12/2008 | Xu et al. | |
| 2009/0109187 | A1 | 4/2009 | Noma | |
| 2009/0160792 | A1 | 6/2009 | Morohoshi et al. | |
| 2009/0295743 | A1 | 12/2009 | Nakajoh | |
| 2010/0013780 | A1* | 1/2010 | Ikeda et al. | 345/173 |
| 2010/0085317 | A1* | 4/2010 | Park | G06F 1/1626 345/173 |
| 2010/0241985 | A1* | 9/2010 | Kim et al. | 715/773 |
| 2010/0277414 | A1* | 11/2010 | Tartz et al. | 345/169 |
| 2010/0315356 | A1 | 12/2010 | Ferren et al. | |
| 2011/0065482 | A1* | 3/2011 | Koide | A61B 5/02438 455/566 |
| 2011/0102334 | A1* | 5/2011 | Colley | G06F 3/0418 345/173 |
| 2012/0030624 | A1* | 2/2012 | Migos | 715/830 |
| 2012/0075194 | A1* | 3/2012 | Ferren | 345/168 |
| 2012/0162078 | A1* | 6/2012 | Ferren et al. | 345/168 |
| 2012/0306788 | A1* | 12/2012 | Chen | G06F 3/0482 345/173 |
| 2013/0296714 | A1* | 11/2013 | Kassim | A61B 5/6898 600/479 |

FOREIGN PATENT DOCUMENTS

| | | |
|---|---|---|
| JP | H10-314134 A | 12/1998 |
| JP | 2003-225214 A | 8/2003 |
| JP | 04-119863 B2 | 7/2008 |
| JP | 2009-509234 A | 3/2009 |
| JP | 2009-163278 A | 7/2009 |
| JP | 2011-008767 A | 1/2011 |
| JP | 2011-118729 A | 6/2011 |
| WO | WO 02/33846 A1 | 4/2002 |
| WO | WO-2005-048832 A1 | 6/2005 |
| WO | WO-2010-147611 A1 | 12/2010 |

\* cited by examiner

MOBILE APPARATUS

CROSS REFERENCE TO RELATED APPLICATIONS

The present application is a continuation of International Application No. PCT/JP2012/003224, filed May 17, 2012, which claims priority to Japanese Patent Application No. 2011-140571, filed Jun. 24, 2011, the entire contents of each of which are incorporated herein by reference.

FIELD OF THE INVENTION

The present invention relates to mobile apparatuses and specifically to mobile apparatuses including a biosensor for obtaining biosignals.

BACKGROUND OF THE INVENTION

In recent years, people have been increasingly interested in maintaining or improving their health. Hence, it is desired that one can more easily obtain biological information such as a pulse rate and an electrocardiogram in a daily life for health management. Patent Document 1 discloses a cellular phone that can detect biological information in the normal process of using the phone. Further, Patent Document 2 discloses a cellular phone that allows a user to measure biological information such as body temperature.

The cellular phone disclosed in Patent Document 1 includes galvanic skin reflex (GSR) sensors arranged on the side surface portions of the two peripheral surfaces, corner portions, or the operation surfaces of input buttons, of the cellular phone. Hence, with this cellular phone, biological information can be obtained through normal operations, for example, for voice communication and email communication, i.e., without performing explicit operations for obtaining the biological information.

On the other hand, the cellular phone disclosed in Patent Document 2 includes a contact detection unit that has a pair of electrodes and detects the contact state of a human body and a temperature detection unit for measuring body temperature as biological information of a human body, arranged on the right side surface of the casing of the main body. With this cellular phone, information about the body temperature of a user detected by the temperature detection unit is obtained when it is detected that the user is in contact with the temperature detection unit on the basis of a current flowing through the pair of electrodes forming part of the contact detection unit. Hence, with this cellular phone, body temperature information is automatically obtained while a user is in contact with the contact detection unit without performing a special operation, such as an operation of turning on a measurement initiation switch.

Patent Document 1: International Publication No. 2005/048832

Patent Document 2: Japanese Patent No. 4119863

As described above, with the cellular phone disclosed in Patent Document 1 and the cellular phone disclosed in Patent Document 2, the biological information of a user can be obtained while the user is holding the cellular phone and performing normal operations, such as an operation of entering/selecting a telephone number and an operation of writing an electronic mail. However, even when a biosensor is provided at a position with which the hand of a user is in contact while the user is operating a mobile apparatus such as a cellular phone, during actual operations, a portion other than a finger used for the operations will also move together with the finger, thereby causing a problem in that noise is superimposed on the output signal of the biosensor.

In particular, when a measured portion is a portion of a hand which performs the operation, noise superimposed on the sensor output signal may become larger than a biosignal, thereby making the measurement impossible. In addition, when a pulse rate and a heartbeat are measured, obtaining of data in real time or obtaining of continuous data over a relatively long time (for example, about ten seconds to several minutes) is required in many cases, thereby causing an increase in the influence of body movement noise.

SUMMARY OF THE INVENTION

In view of solving the problems described above, in a mobile apparatus provided with a biosensor for obtaining a biosignal, it is an object of the present invention to provide a mobile apparatus that allows body movement noise generated by body movement at the time of operating the mobile apparatus with a finger to be decreased, when a biosignal is obtained while the mobile apparatus is being used while held in the hand.

A mobile apparatus according to the present invention is a mobile apparatus that is capable of being held in a hand and operated with a thumb, and that includes: a biosensor obtaining a biosignal from a hand holding the mobile apparatus; and an operation switch accepting an operation performed by a thumb. The operation switch is arranged along a circular arc of a virtual circle whose center is located at a carpometacarpal joint of the thumb of a hand performing the operation and whose radius is a distance from the carpometacarpal joint to a tip of the thumb.

According to mobile apparatus of the present invention, the operation switch is arranged along a circular arc of a virtual circle whose center is located at a carpometacarpal joint of the thumb performing the operation and whose radius is a distance from the carpometacarpal joint to a tip of the thumb. As a result, during the operation performed by the thumb, movements, together with the thumb, of fingers other than the thumb and the palm are suppressed. Hence, body movement noise generated by body movement at the time of operating the mobile apparatus with a finger can be decreased, when a biosignal is obtained while the mobile apparatus is being used while held in the hand.

A mobile apparatus according to the present invention is a mobile apparatus that is capable of being held in a hand and operated with a finger, and that includes: a biosensor obtaining a biosignal from a hand holding the mobile apparatus; and an operation switch accepting an operation performed by a finger. The operation switch, when a biosignal is obtained by the biosensor, does not accept an operation performed by the finger of the hand from which the biosignal is being obtained.

According to the mobile apparatus of the present invention, when a biosignal is obtained by the biosensor, the operation switch does not accept an operation performed by a finger of the hand from which the biosignal is being obtained. As a result, operations are performed with a finger of a hand different from the hand from which a biosignal is being obtained. Hence, when a biosignal is obtained, body movement noise generated by body movement at the time of operating the mobile apparatus with a finger can be further decreased, whereby a stable biosignal can be obtained during the operation of the mobile apparatus.

Note that at this time, it is preferable that the operation switch be arranged along a circular arc of a virtual circle whose center is located at a carpometacarpal joint of a thumb of a hand performing the operation and whose radius is a distance from the carpometacarpal joint to a tip of the thumb.

A mobile apparatus according to the present invention is a mobile apparatus that is capable of being held in a hand and operated with a finger, and that includes: a plurality of biosensors obtaining biosignals respectively from a left hand and a right hand holding the mobile apparatus; biosignal selection means selectively outputting biosignals obtained by the respective biosensors; operation switches accepting respective operations performed by a finger of the right hand and a finger of the left hand; and operation frequency obtaining means obtaining operation frequencies of respective switch operations performed by the right hand and the left hand. The biosignal selection means preferentially selects and outputs a biosignal obtained from a hand, among the right and left hands, whose operation frequency obtained by the operation frequency obtaining means is lower.

According to the mobile apparatus of the present invention, a biosignal obtained from a hand, among the right and left hands, whose operation frequency is lower is preferentially selected and output. Hence, an influence from body movement noise generated by body movement at the time of operating the mobile apparatus with a finger can be further reduced.

A mobile apparatus according to the present invention is a mobile apparatus that is capable of being held in a hand and operated with a finger, and that includes: a biosensor obtaining a biosignal from a hand holding the mobile apparatus; and operation switches which accept operations performed by a finger and whose arrangement is capable of being changed; and switch arrangement changing means changing the arrangement of the operation switches. The switch arrangement changing means, when a biosignal is obtained by the biosensor, changes the arrangement of the operation switches in such a manner that an operation switch that accepts an operation performed by a finger of a hand from which the biosignal is being obtained is not present.

According to the mobile apparatus of the present invention, when a biosignal is obtained by the biosensor, the arrangement of the operation switches is changed in such a manner that an operation switch that accepts an operation performed by a finger of a hand from which the biosignal is being obtained is not present. As a result, since an operation is performed with a hand different from the hand from which a biosignal is being obtained, body movement noise generated by body movement at the time of operating the mobile apparatus with a finger can be further decreased, whereby a stable biosignal can be obtained during the operation of the mobile apparatus.

Note that it is preferable that the switch arrangement changing means, when a biosignal is obtained by the biosensor, arrange the operation switches along a circular arc of a virtual circle whose center is located at a carpometacarpal joint of a thumb of a hand from which the biosignal is not being obtained and whose radius is a distance from the carpometacarpal joint to a tip of the thumb.

A mobile apparatus according to the present invention is a mobile apparatus that is capable of being held in a hand and operated with a thumb, and that includes: a biosensor obtaining a biosignal from a hand holding the mobile apparatus; an operation switch which accepts an operation performed by a thumb and arrangement of which is capable of being changed; and switch arrangement changing means changing the arrangement of the operation switch. The switch arrangement changing means, when a biosignal is obtained by the biosensor, changes the arrangement of the operation switch in such a manner that the operation switch is arranged along a circular arc of a virtual circle whose center is located at a carpometacarpal joint of the thumb of a hand performing an operation and whose radius is a distance from the carpometacarpal joint to a tip of the thumb.

According to the mobile apparatus of the present invention, when a biosignal is obtained from a hand of a user, the arrangement of the operation switch is changed in such a manner that the operation switch is arranged along a circular arc of a virtual circle whose center is located at a carpometacarpal joint of the thumb of the hand performing an operation and whose radius is a distance from the carpometacarpal joint to a tip of the thumb. Hence, during the operation performed by the thumb, movements, together with the thumb, of fingers other than the thumb and the palm are suppressed. Hence, when a biosignal is obtained while the mobile apparatus is used while held in the hand, it is possible to decrease body movement noise generated by body movement at the time of operating the mobile apparatus with the thumb.

A mobile apparatus according to the present invention is a mobile apparatus that is capable of being held in a hand and operated with a thumb, and that includes: a plurality of biosensors obtaining biosignals respectively from a left hand and a right hand holding the mobile apparatus; biosignal selection means selectively outputting biosignals obtained by the respective biosensors; a plurality of operation switches which accept operations performed by respective thumbs of the right and left hands and whose arrangement is capable of being changed; switch arrangement changing means changing the arrangement of the plurality of switches respectively for the right and left hands; and operation frequency obtaining means obtaining operation frequencies of respective switch operations performed by the right hand and the left hand. The switch arrangement changing means, when biosignals are obtained by the biosensors, for each of the right and left hands, changes the arrangement of the operation switches in such a manner that the operation switches are arranged along a circular arc of a virtual circle whose center is located at a carpometacarpal joint of a thumb of the hand and whose radius is a distance from the carpometacarpal joint to a tip of the thumb. The biosignal selection means preferentially selects and outputs a biosignal obtained from a hand, among the right and left hands, whose operation frequency obtained by the operation frequency obtaining means is lower.

According to the mobile apparatus of the present invention, when biosignals are obtained, for each of the right and left hands, the switch arrangement changing means changes the arrangement of the operation switches in such a manner that the operation switches are arranged along a circular arc of a virtual circle whose center is located at a carpometacarpal joint of a thumb of the hand and whose radius is a distance from the carpometacarpal joint to a tip of the thumb. Hence, during the operation performed by the thumb, movements, together with the thumb, of fingers other than the thumb and the palm are suppressed, and it is possible to decrease body movement noise generated by body movement at the time of operating the mobile apparatus with the thumb. Further, according to the mobile phone of the present invention, a biosignal obtained from a hand, among the right and left hands, whose operation frequency obtained by the operation frequency obtaining means is lower is preferentially selected and output. Hence, it is possible to further decrease the influence of body movement noise generated by body movement at the time of operating the mobile apparatus with the thumb.

A mobile apparatus according to the present invention is a mobile apparatus that is capable of being held in a hand and operated with a thumb, and that includes: holding hand determination means determining which hand/hands are holding the mobile apparatus; a biosensor obtaining a biosignal from a hand holding the mobile apparatus; an operation switch which accepts an operation performed by a thumb and arrangement of which is capable of being changed; and switch arrangement changing means changing the arrangement of the operation switch. The switch arrangement changing means, when a biosignal is obtained by the biosensor, in a case in which it is determined by the holding hand determination means that the mobile apparatus is held in a single hand, changes the arrangement of the operation switch in such a manner that the operation switch is arranged along a circular arc of a virtual circle whose center is located at a carpometacarpal joint of a thumb of the hand holding the mobile apparatus and whose radius is a distance from the carpometacarpal joint to a tip of the thumb of the hand holding the mobile apparatus.

According to the mobile apparatus of the present invention, the arrangement of the operation switch is changed in such a manner that the operation switch is arranged along a circular arc of a virtual circle whose center is located at a carpometacarpal joint of a thumb of the hand holding the mobile apparatus and whose radius is a distance from the carpometacarpal joint to a tip of the thumb of the hand. Hence, even when the mobile apparatus is operated while being held in a single hand, during the operation performed by the thumb, movements, together with the thumb, of fingers other than the thumb and the palm are suppressed, and it is possible to decrease body movement noise generated by body movement at the time of operating the mobile apparatus with the thumb.

In the mobile apparatus according to the present invention, it is preferable that the mobile apparatus further include: position information obtaining means obtaining position information of a region touched by the thumb; arrangement region setting means setting a target arrangement region of the operation switch on the basis of the position information obtained by the position information obtaining means, and the switch arrangement changing means arrange the operation switch in such a manner that an overlapping/corresponding area of the operation switch and the target arrangement region set by the arrangement region setting means becomes larger.

In general, the size of a user's hand or the way the user holds the apparatus varies with the user. In this case, since the operation switch is arranged in such a manner that an overlapping/corresponding area of the operation switch and the target arrangement region set on the basis of the position information of a touched region becomes larger, for example, the operation switch can be arranged in accordance with the size of the user's hand or the way the user holds the apparatus. In other words, the operation switch can be arranged at the optimal position for each user. As a result, it is possible to further decrease body movement noise generated by body movement at the time of operating the mobile apparatus with the thumb.

According to the present invention, in a mobile apparatus including a biosensor for obtaining a biosignal, body movement noise generated by body movement at the time of operating the mobile apparatus with a finger can be decreased, when a biosignal is obtained while the mobile apparatus is being used while held in the hand.

DETAILED DESCRIPTION OF THE PREFERRED EMBODIMENTS OF THE INVENTION

Hereinafter, preferred embodiments of the present invention will be described in detail with reference to the drawings. Note that components common in the figures are denoted by the same reference symbols and duplicate descriptions thereof are omitted.

First Embodiment

Figure 1:
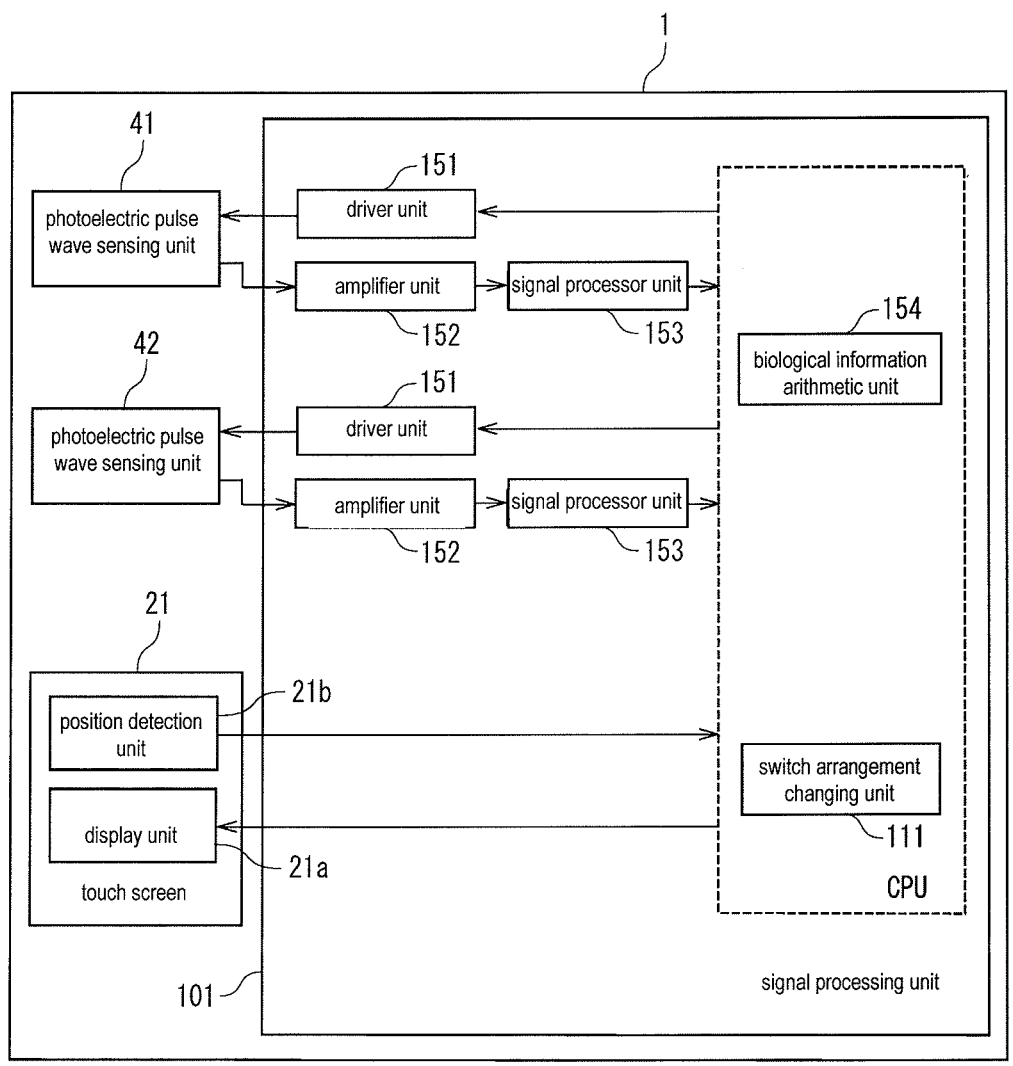
FIG. 1 is a block diagram illustrating the configuration of a mobile apparatus according to a first embodiment.
Figure 2:
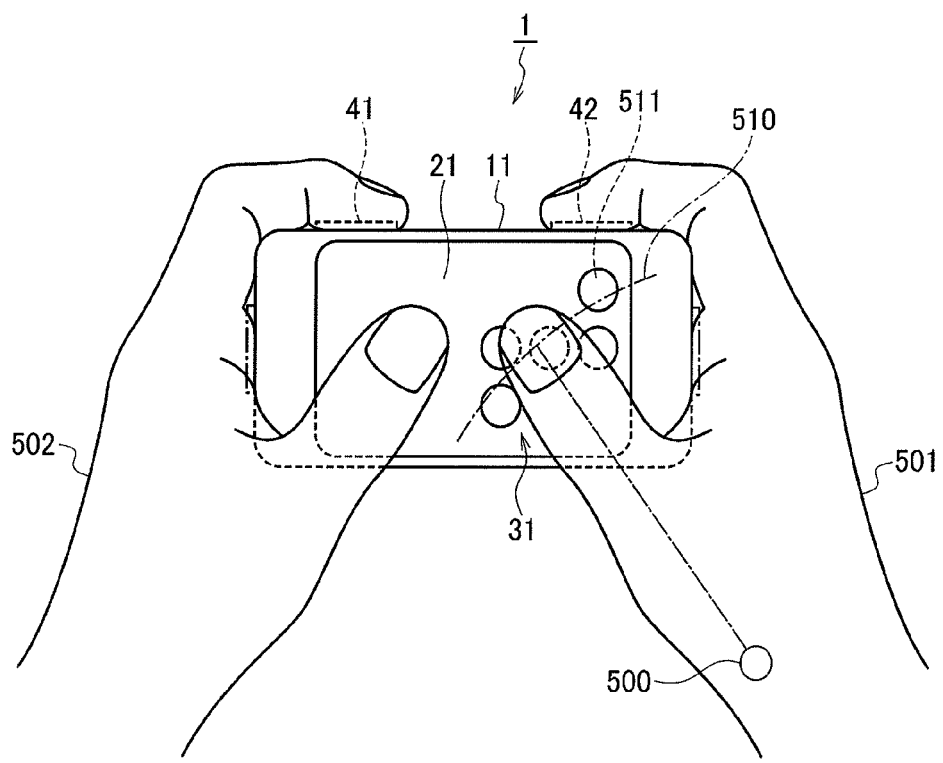
FIG. 2 is a diagram illustrating the arrangement of operation switches of the mobile apparatus according to the first embodiment at the time when a biosignal is obtained.

First, referring to FIG. 1 as well as FIG. 2, the configuration of a mobile apparatus 1 according to a first embodiment will be described. FIG. 1 is a block diagram illustrating the configuration of the mobile apparatus 1. FIG. 2 is a diagram illustrating the arrangement of operation switches at the time when a biosignal is obtained.

The mobile apparatus 1 is an electronic apparatus which is used (operated) while held in a hand, for example, a cellular phone, a smart phone, a mobile PC such as a tablet PC, a mobile apparatus such as a handheld game console, a remote controller, or the like. Specifically, the mobile apparatus 1 is an electronic apparatus which is held in a hand and the switches thereof are operated with a thumb, for example. Note that a smart phone will be described as an example of the mobile apparatus 1 in the present embodiment (hereinafter, a mobile apparatus is also called a "smart phone").

The smart phone 1 includes biosignal sensing units (corresponding to the biosensors described in the claims) 41 and 42 for obtaining a biosignal, and is configured to be able to obtain a biosignal while the smart phone 1 is used while held in a hand. For example, in the smart phone 1, the biological information of a user can be obtained while the user is holding the smart phone 1 and performing normal operations, such as use of a search engine, an operation of entering/selecting a telephone number, and an operation of writing an electronic mail.

The smart phone 1 has a function of arranging operation switches 31 along a circular arc 510 of a virtual circle whose center is located at a carpometacarpal joint 500 of the thumb of a hand 501 performing operations and whose radius is the distance from the carpometacarpal joint 500 to the tip of the thumb, while biosignals are obtained by the biosignal sensing units 41 and 42.

For this purpose, the smart phone 1 includes the biosignal sensing units 41 and 42 for obtaining the biosignals of a user, a signal processing unit 101 that processes the obtained biological signals, obtains and stores biological information, and generates and outputs a signal for changing the arrangement of a plurality of the operation switches 31, and a touch screen 21 for displaying the operation switches 31. The signal processing unit 101 includes driver units 151, amplifier units 152, signal processor units 153, a biological information arithmetic unit 154, a switch arrangement changing unit 111, and the like. The configurations will be described in detail below.

The biosignal sensing units 41 and 42 each obtain a biosignal from a finger or a palm holding the apparatus. Examples of a biosensor used include a photoelectric pulse wave sensor, an oxygen saturation sensor, a pressure pulse wave sensor, a cardiogram sensor, a myoelectric sensor, a skin resistance sensor, a sweat sensor, a skin temperature sensor, and a body fat sensor. In the present embodiment, photoelectric pulse wave sensors that can obtain biological information are used as the biosignal sensing units 41 and 42 that can obtain biological information such as a pulse rate as a result of being touched by a fingertip (hereinafter, the biosignal sensing unit is also called a "photoelectric pulse wave sensing unit"). A photoelectric pulse wave sensor optically measures a pulse rate and the like utilizing the light absorption characteristics of hemoglobin in blood.

Note that the sensors used as the biosignal sensing units 41 and 42 are not limited to photoelectric pulse wave sensors, and may be sensors selected from, for example, the biosensors described above in accordance with a biosignal to be obtained. At this time, the biosignal sensing unit 41 and the biosignal sensing unit 42 may use sensors of the same type or may use different types of sensor. For example, when a photoelectric pulse wave sensor and a cardiogram sensor are used in combination, a cardiogram signal can be obtained at the same time in addition to a pulse rate. Further, the number of biosignal sensing units attached to the smart phone 1 is not limited to two and may be one or may be three or more.

It is preferable that, when the smart phone 1 is held in two hands 501 and 502, the photoelectric pulse wave sensing units 41 and 42 be arranged in locations of the smart phone 1 with each of which an index finger, a middle finger, or a portion of a palm near the bases of the fingers is in contact, for example, the two side surfaces of a main body 11 of the smart phone 1 (refer to the portions indicated by one-dot chain lines in FIG. 2), the vicinity of the two end portions of the top surface, or the vicinity of the two side surfaces on the back surface. Note that in the present embodiment, the photoelectric pulse wave sensing units 41 and 42 are located on the two end portions of the top surface of the smart phone 1, as illustrated in FIG. 2.

The touch screen 21 is attached to the front surface of the main body 11 of the smart phone 1. The touch screen 21 includes a display unit 21a which is formed of a liquid crystal display (LCD) or the like displaying an operation screen and a position detection unit 21b formed of a touch panel or the like detecting a position (an operation) touched by a user. The display unit 21a, upon receipt of display screen information output from the signal processing unit 101, displays the plurality (five in the example of FIG. 2) of various operation switches 31 for operation of the apparatus and various types of information. The position detection unit 21b is provided in such a manner as to cover the display screen of the display unit 21a, and on the surface thereof, two-dimensional coordinates (X-Y coordinates) are virtually arranged. When a touch operation is performed by a user, the position detection unit 21b outputs coordinate information in accordance with the touched position. Note that the detection of a touched position is performed using, for example, electrical resistance, pressure, capacitance, infrared rays, or ultrasonic waves.

The touch screen 21, which is connected to the signal processing unit 101, outputs the detected coordinate information of a touched position to the signal processing unit 101. Then on the basis of the display positions of the operation switches 31 and the coordinate information indicating a touched position, the content of the user operations is determined by the signal processing unit 101.

The signal processing unit 101, as described above, includes the driver units 151, the amplifier units 152, the signal processor units 153, the biological information arithmetic unit 154, the switch arrangement changing unit 111, and the like. The signal processing unit 101 processes photoelectric pulse wave signals obtained by the photoelectric pulse wave signal sensing units 41 and 42 and obtains biological information of a user, such as a pulse rate. Further, the signal processing unit 101, when photoelectric pulse wave signals are obtained by the photoelectric pulse wave sensing units 41 and 42, changes the arrangement of the operation switches 31 displayed on the touch screen 21 (the display unit 21a). The details will be described later.

For this purpose, the signal processing unit 101 includes the driver units 151 that drive light emitting devices, such as LEDs and VCSELs, forming the photoelectric pulse wave signal sensing units 41 and 42, the amplifier units 152 functioning as input interfaces, the signal processor units 153, a microprocessor that performs arithmetic operations on photoelectric pulse wave signals input through the amplifier units 152 and the signal processing units 153, a ROM storing programs and data for causing the microprocessor to perform various kinds of processing, a RAM temporarily storing various kinds of data such as arithmetic operation results, a backup RAM in which backup data is stored, and the like. In the signal processing unit 101, the functions of the biological information arithmetic unit 154 and the switch arrangement changing unit 111 are realized as a result of the programs stored in the ROM being executed by the microprocessor.

The amplifier units 152, which are formed of amplifiers that use, for example, operational amplifiers, amplify photoelectric pulse wave signals detected by photo acceptance devices such as photo diodes and photo transistors that form the photoelectric pulse wave sensing units 41 and 42. The photoelectric pulse wave signals amplified by the amplifier units 152 are output to the signal processor units 153. The signal processor units 153 process the photoelectric pulse wave signals, which have been amplified by the amplifier units 152 and subjected to an A/D conversion process, and output the signals to the biological information arithmetic unit 154. Note that a configuration may be employed in which noise is removed from each of the photoelectric pulse wave signals using, for example, a low pass filter or a band pass filter as preprocessing. Alternatively, noise may be removed through filtering processing after the A/D conversion, using a digital filter.

The biological information arithmetic unit 154 obtains pulse information from the read photoelectric pulse wave signal. Note that the obtained biological information, such as pulse information is output to the outside or stored in the RAM described above.

The switch arrangement changing unit 111, as illustrated in FIG. 2, when photoelectric pulse wave signals are obtained by the photoelectric pulse wave sensing units 41 and 42, changes the arrangement of the operation switches 31 displayed on the touch screen 21 in such a manner that the operation switches 31 are arranged along the circular arc 510 of a virtual circle whose center is located at the carpometacarpal joint 500 of the thumb of a hand (the right hand 501 in the example of FIG. 2) performing operations and whose radius is the distance from the carpometacarpal joint 500 to the tip of the thumb. In other words, the switch arrangement changing unit 111 functions as the switch arrangement changing means. Here, for example, the hand which is performing operations is detected on the basis of the coordinate information of a touched position detected by the position detection unit 21b forming part of the touch screen 21. Note that the position of the carpometacarpal joint 500 of the hand (the right hand 501 in the example of FIG. 2) performing operations and the circular arc 510 of a virtual circle whose center is located at the carpometacarpal joint 500 and whose radius is the distance from the carpometacarpal joint 500 to the tip of the thumb, are set in advance on the basis of stochastic data such as the standard size of a hand, the standard lengths of fingers, and manners in which the smart phone 1 is held.

Note that the arrangement of the operation switches 31 may be changed with the following signals as triggers: a signal from the photoelectric pulse wave sensing unit 41 or the photoelectric pulse wave sensing unit 42, a signal of a proximity switch that detects contact with a finger or the palm of a hand, or a signal of an ON/OFF switch that controls the start/stop of the measurement of photoelectric pulse wave signals.

Although FIG. 2 illustrates the case in which the operation switches 31 are pressed using the thumb of the right hand 501, in the case where the operation switches are pressed using the left hand 502, the switch arrangement changing unit 111 changes the arrangement of the switches displayed on the touch screen 21 to arrangement which is a mirror image of FIG. 2, in which right and left are reversed, i.e., the operation switches are arranged along a circular arc of a virtual circle whose center is located at the carpometacarpal joint of the thumb of the left hand 502 and whose radius is the distance from the carpometacarpal joint to the tip of the thumb.

Figure 3:
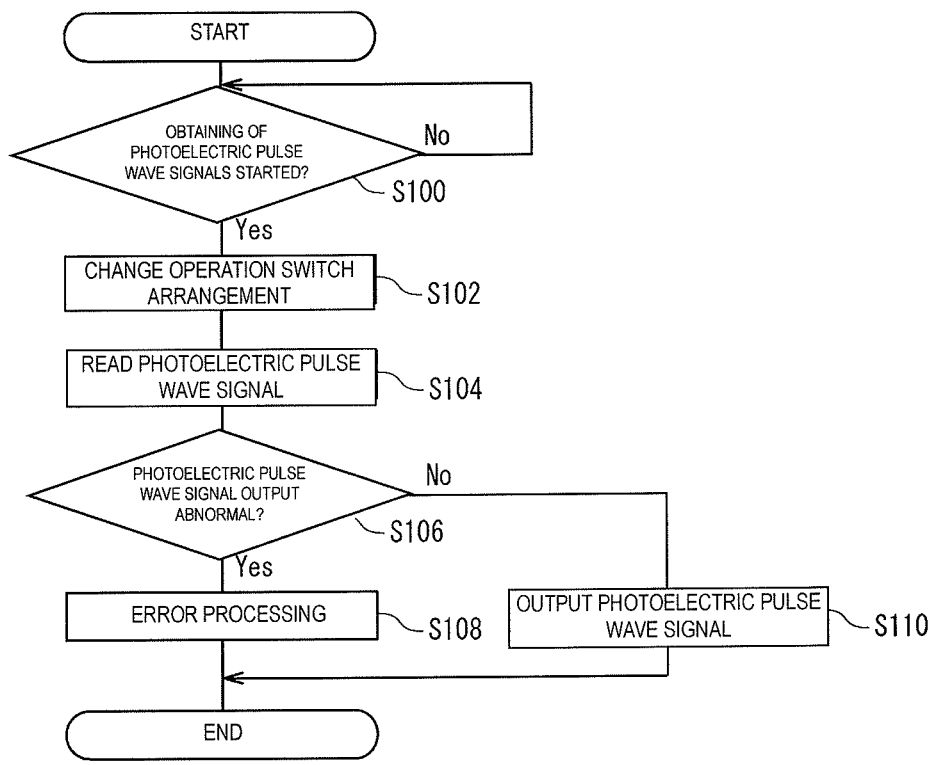
FIG. 3 is a flowchart illustrating the processing steps of biosignal measurement processing performed by the mobile apparatus according to the first embodiment.

Next the operation of the smart phone 1 will be described with reference to FIG. 3. FIG. 3 is a flowchart illustrating the processing steps of biosignal measurement processing performed by the smart phone 1. Note that this processing is performed in the signal processing unit 101 at a predetermined timing.

In step S100, it is determined whether or not the finger tips of a user have touched the photoelectric pulse wave sensing units 41 and 42 and a process of obtaining a photoelectric pulse wave signal has been started. Here, when it is determined that the process of obtaining a photoelectric pulse wave signal has been started, the flow proceeds to step S102. On the hand, when it is determined that the process of obtaining a photoelectric pulse wave signal has not been started, the present step is repeated until the finger tips of a user touch the photoelectric pulse wave sensing units 41 and 42 and a process of obtaining a photoelectric pulse wave signal is started.

In step S102, the arrangement of the plurality of operation switches 31 displayed on the touch screen 21 is changed. More specifically, the arrangement of the operation switches 31 displayed on the touch screen 21 is changed in such a manner that the operation switches 31 are arranged along the circular arc 510 of a virtual circle whose center is located at the carpometacarpal joint 500 of the thumb of a hand (the right hand 501 in the example of FIG. 2) performing operations and whose radius is the distance from the carpometacarpal joint 500 to the tip of the thumb.

Then in step S104, the obtained photoelectric pulse wave signal is read. In step S106 that follows, an error check (for example, whether or not the voltage of the signal is within a predetermined range) is performed for the read photoelectric pulse wave signal.

Here, when it is determined that the photoelectric pulse wave signal is abnormal (that is, determined that an error has occurred), the data is discarded in step S108 and then the present processing is temporarily stopped. On the other hand, when it is determined that the read photoelectric pulse wave signal is normal, the data is output to the biological information arithmetic unit 154 in step S110. Then the present processing is temporarily stopped.

According to the present embodiment, when a photoelectric pulse wave signal is obtained, the arrangement of the operation switches 31 is changed in such a manner that the operation switches 31 are arranged along the circular arc 510 of a virtual circle whose center is located at the carpometacarpal joint 500 of the thumb of the hand 501 performing operations and whose radius is the distance from the carpometacarpal joint 500 to the tip of the thumb. Hence, during the operation performed by the thumb, movements, together with the thumb, of fingers other than the thumb and the palm are suppressed. Hence, when a photoelectric pulse wave signal is obtained while the smart phone 1 is used while held in the hand, it is possible to decrease body movement noise generated by body movement at the time of operating the smart phone 1 with the thumb.

Further, according to the present embodiment, the arrangement of the operation switches 31 can be changed in such a manner that the operation switches 31 are arranged along the circular arc 510 of a virtual circle whose center is located at the carpometacarpal joint 500 of the thumb of the hand 501 whose photoelectric pulse wave signal is not obtained and whose radius is the distance from the carpometacarpal joint 500 to the tip of the thumb. In this case, since operations are performed using the thumb of the hand 501 different from the hand 502 whose photoelectric pulse wave information is obtained, when a photoelectric pulse wave signal is obtained, it is possible to further decrease body movement noise generated by body movement at the time of operating the smart phone 1 with the thumb, whereby a photoelectric pulse wave signal can be stably obtained during the operation of the smart phone 1.

Second Embodiment

Figure 4:
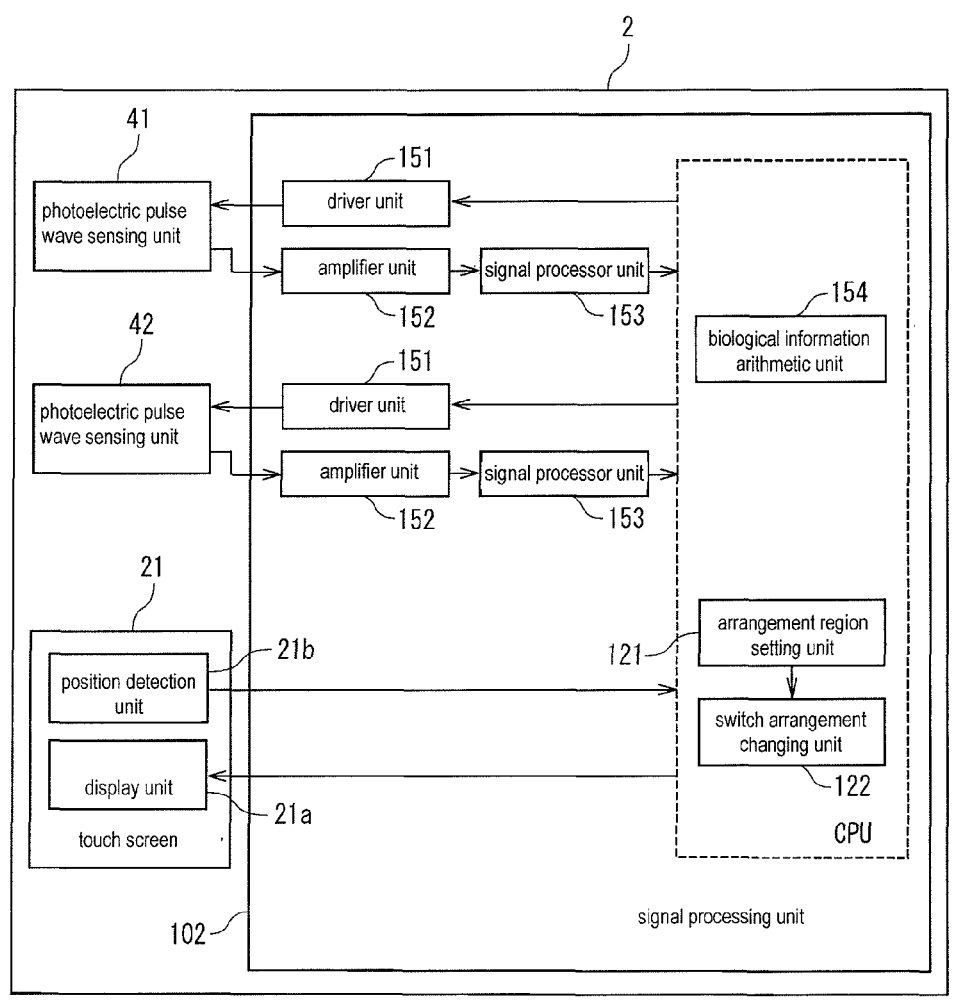
FIG. 4 is a block diagram illustrating the configuration of a mobile apparatus according to a second embodiment.

Next, referring to FIG. 4, the configuration of a smart phone (mobile apparatus) 2 according to a second embodiment will be described. FIG. 4 is a block diagram illustrating the configuration of the smart phone 2. Note that in FIG. 4, components that are the same as or equivalent to those of the first embodiment are denoted by the same reference symbols.

As described above, the position of the carpometacarpal joint 500 of the hand performing operations and the circular arc 510 of a virtual circle whose center is located at the carpometacarpal joint 500 and whose radius is the distance from the carpometacarpal joint 500 to the tip of the thumb, are set in advance on the basis of stochastic data such as the standard size of a hand, the standard lengths of fingers, and a standard manner in which the smart phone 1 is held. However, the optimum arrangement of the switches varies in accordance with, for example, the size of a user's hand or the way the user holds the apparatus.

The smart phone 2 includes an additional function of changing the arrangement of the operation switches 31 in accordance with a user, compared with the smart phone 1 described above. Hence, the smart phone 2 includes a signal processing unit 102 instead of the signal processing unit 101 described above. Unlike the signal processing unit 101, the signal processing unit 102 includes an arrangement region setting unit 121 in addition to the configuration of the signal processing unit 101. Further, unlike the signal processing unit 101, the signal processing unit 102 includes a switch arrangement changing unit 122 instead of the switch arrangement changing unit 111. The rest of the configuration is the same as or similar to that of the smart phone 1 and, hence, the detailed description thereof is omitted here.

Figure 6:
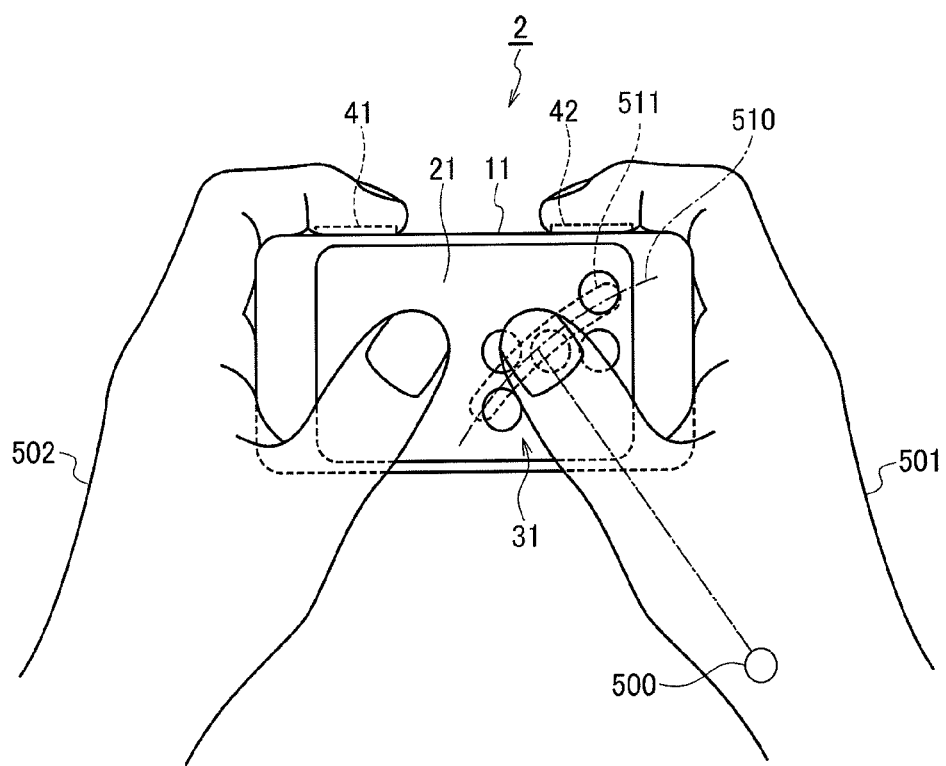
FIG. 6 is a diagram illustrating a method of arranging operation switches performed by the mobile apparatus according to the second embodiment.

As described above, the position detection unit 21b forming part of the touch screen 21, in response to a user's touch operation, detects position (coordinate) information corresponding to the touched position. Here, for example, at the time of a first operation, in the case in which a region where a thumb is likely to move is input through the touch screen 21 as illustrated in FIG. 6, the position detection unit 21b detects the position information of a region 511 touched by the thumb. In other words, the touch screen 21 (the position detection unit 21b) functions as the position information obtaining means. Note that the position information of the region 511 detected by the position detection unit 21b is output to the signal processing unit 102.

The arrangement region setting unit 121 in the signal processing unit 102 sets the target arrangement region of the operation switches 31 on the basis of the position information of the region 511 touched by the thumb, received from the position detection unit 21b. In other words, the arrangement region setting unit 121 functions as the arrangement region setting means. Note that the target arrangement region may be obtained, for example, by accumulating the input regions touched by the thumb a predetermined number of times. The set target arrangement region is output to the switch arrangement changing unit 122.

The switch arrangement changing unit 122 arranges the (group of) operation switches 31 in such a manner that an overlapping/corresponding area of the (group of) operation switches 31 and the target arrangement region set by the arrangement region setting unit 121 becomes larger. The obtained arrangement information of the (group of) operation switches 31 is output to the display unit 21a forming part of the touch screen 21 and based thereon the (group of) operation switches 31 are arranged and displayed.

Figure 5:
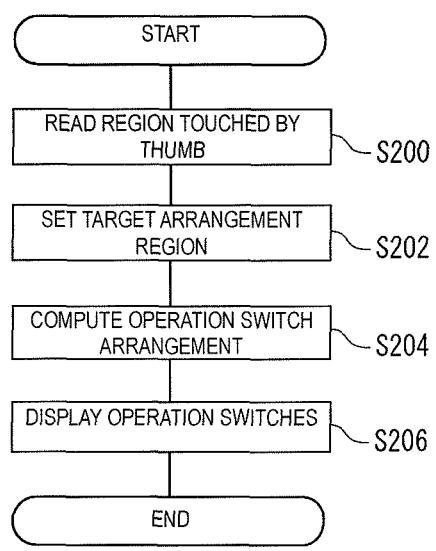
FIG. 5 is a flowchart illustrating the processing steps of operation switch arrangement processing performed by the mobile apparatus according to the second embodiment.

Next, the operation of the smart phone 2 will be described with reference to FIG. 5. FIG. 5 is a flowchart illustrating the processing steps of operation switch arrangement processing performed by the smart phone 2. Note that this processing is performed at a predetermined timing in the signal processing unit 102.

In step S200, the position (coordinate) information of the region 511 touched by the thumb, output from the position detection unit 21b forming part of the touch screen 21, is read.

Then, in step S202, the target arrangement region of the group of operation switches 31 is set on the basis of the position information of the region 511 touched by the thumb, read in step S200.

Next, in step S204, the arrangement of the (group of) operation switches 31 on the touch screen 21 is computed in such a manner that an overlapping/corresponding area of the (group of) operation switches 31 and the target arrangement region set in step S202 becomes larger.

Then, in step S206, the (group of) operation switches 31 are displayed at positions on the touch screen 21 obtained in step S204.

According to the present embodiment, the operation switches 31 are arranged in such a manner that an overlapping/corresponding area of the operation switches 31 and the target arrangement region set on the basis of the position information of the region 511 touched by the thumb becomes larger. Hence, the operation switches 31 can be arranged, for example, in accordance with the size of a user's hand or the way the user holds the smart phone. In other words, the operation switches 31 can be arranged at the optimal positions for each user. As a result, it is possible to more efficiently decrease body movement noise generated by body movement at the time of operating the smart phone 2 with the thumb.

Third Embodiment

Figure 7:
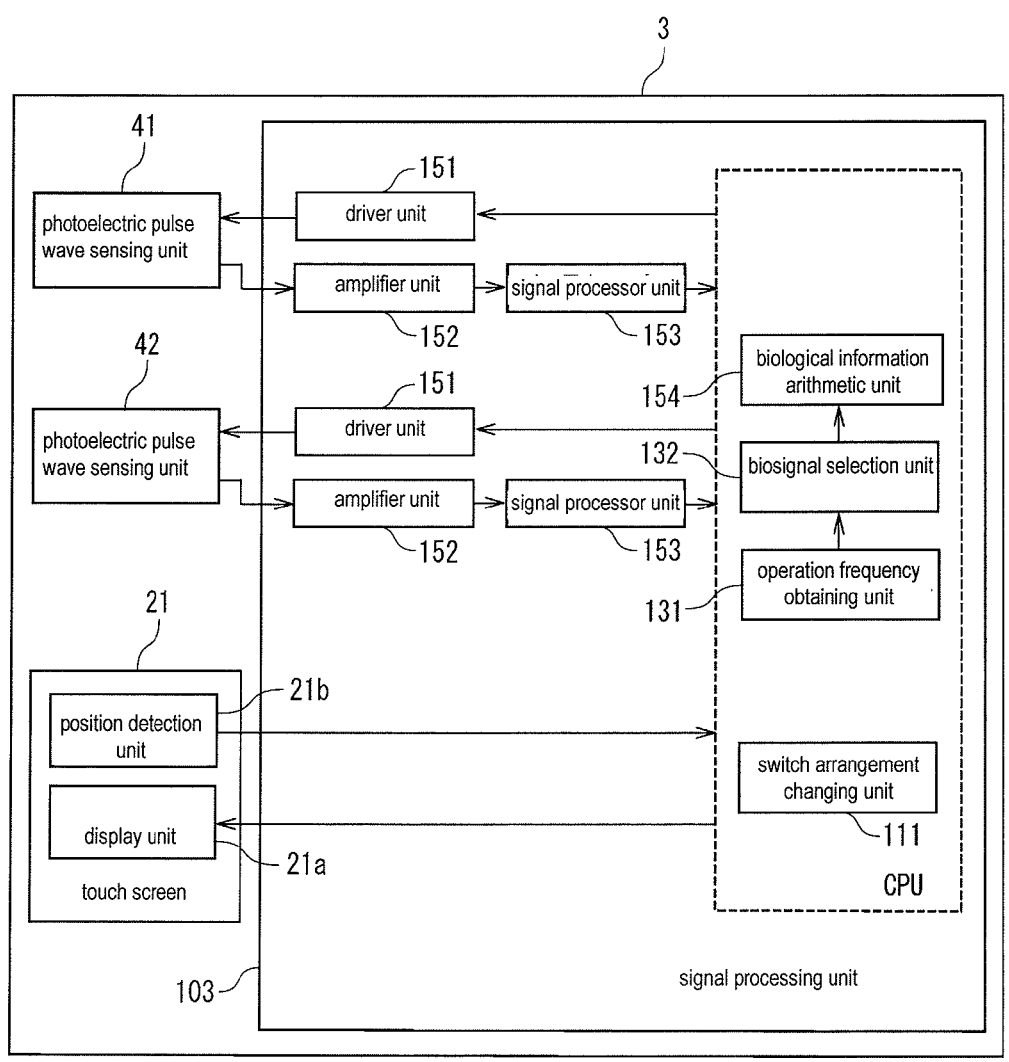
FIG. 7 is a block diagram illustrating the configuration of a mobile apparatus according to a third embodiment.
Figure 8:
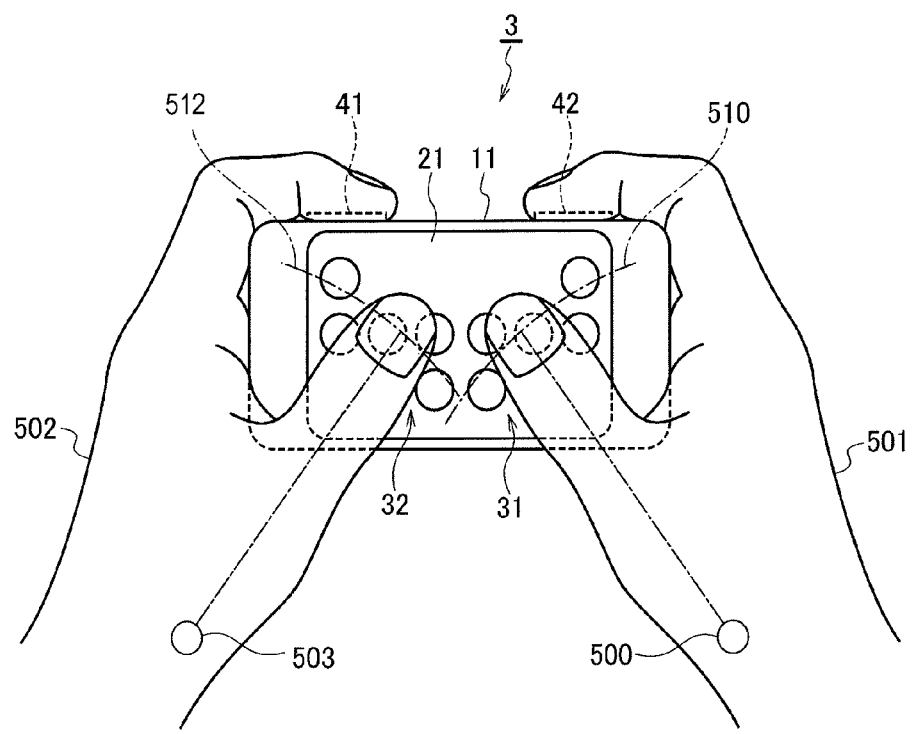
FIG. 8 is a diagram illustrating the arrangement of operation switches of the mobile apparatus according to the third embodiment at the time when biosignals are obtained.

Next, referring to FIG. 7 as well as FIG. 8, the configuration of a smart phone (mobile apparatus) 3 according to a third embodiment will be described. FIG. 7 is a block diagram illustrating the configuration of the smart phone 3. FIG. 8 is a diagram illustrating the arrangement of the operation switches of the smart phone 3 at the time when photoelectric pulse wave signals are obtained. Note that in FIGS. 7 and 8, components that are the same as or equivalent to those of the first embodiment are denoted by the same reference symbols.

Compared with the smart phone 1 described above, the smart phone 3 has an additional function of switching between the photoelectric pulse wave sensing units 41 and 42 that read detection signals in accordance with the frequency of operations of the operation switches 31 performed by the right hand 501 and the frequency of operations of the operation switches 32 performed by the left hand 502. Hence, the smart phone 3 includes a signal processing unit 103 instead of the signal processing unit 101 described above. Hence, unlike the signal processing unit 101, the signal processing unit 103 further includes an operation frequency obtaining unit 131 and a biosignal selection unit 132 in addition to the configuration of the signal processing unit 101. The rest of the configuration is the same as or similar to that of the smart phone 1 and, hence, the detailed description thereof is omitted here.

When photoelectric pulse wave signals are obtained by the photoelectric pulse wave sensing units 41 and 42, the switch arrangement changing unit 111, for the right hand 501 and the left hand 502, changes the arrangement of the operation switches 31 and the operation switches 32 in such a manner that the operation switches 31 and 32 are respectively arranged along the circular arc 510 and a circular arc 512 of virtual circles whose centers are respectively located at the carpometacarpal joint 500 of the right hand 501 and a carpometacarpal joint 503 of the left hand 502 and whose radiuses are respectively the distances from the carpometacarpal joints 500 and 503 to the tips of the thumbs.

The operation frequency obtaining unit 131 obtains the respective frequencies of switch operations performed by the right hand 501 and the left hand 502. In other words, the operation frequency obtaining unit 131 functions as the operation frequency obtaining means. In more detail, the operation frequency obtaining unit 131 obtains the operation frequencies, for example, by counting the numbers of times the operation switches 31 and 32 are respectively pressed during a predetermined time. The operation frequency obtaining unit 131, by setting larger weights to more recent counts, may obtain weighted operation frequencies as the operation frequencies. The operation frequency information of the right and left operation switches 31 and 32 obtained by the operation frequency obtaining unit 131 is output to the biosignal selection unit 132.

The biosignal selection unit 132 selectively outputs one of the photoelectric pulse wave signals respectively obtained by the biosignal sensing units 41 and 42 in accordance with the operation frequency information obtained by the operation frequency obtaining unit 131. Specifically, the biosignal selection unit 132 selects and outputs the photoelectric pulse wave signal obtained from one of the two right and left hands 501 and 502 whose operation frequency obtained by the operation frequency obtaining unit 131 is lower than that of the other. In other words, as illustrated in FIG. 8, the biosignal selection unit 132 preferentially selects the detection signal of the photoelectric pulse wave sensing unit 42 for the right hand 501 when the left hand 502 side operation switches 32 are being operated, and preferentially selects the detection signal of the photoelectric pulse wave sensing unit 41 for the left hand 502 when the right hand 501 side operation switches 31 are being operated. The biosignal selection unit 132 functions as the biosignal selection means.

Note that it is preferable that sampling of a photoelectric pulse wave signal be always performed by the two photoelectric pulse wave sensing units 41 and 42. The detection signal selected by the biosignal selection unit 132 is output to the biological information arithmetic unit 154, whereby biological information such as a pulse rate is obtained.

Figure 9:
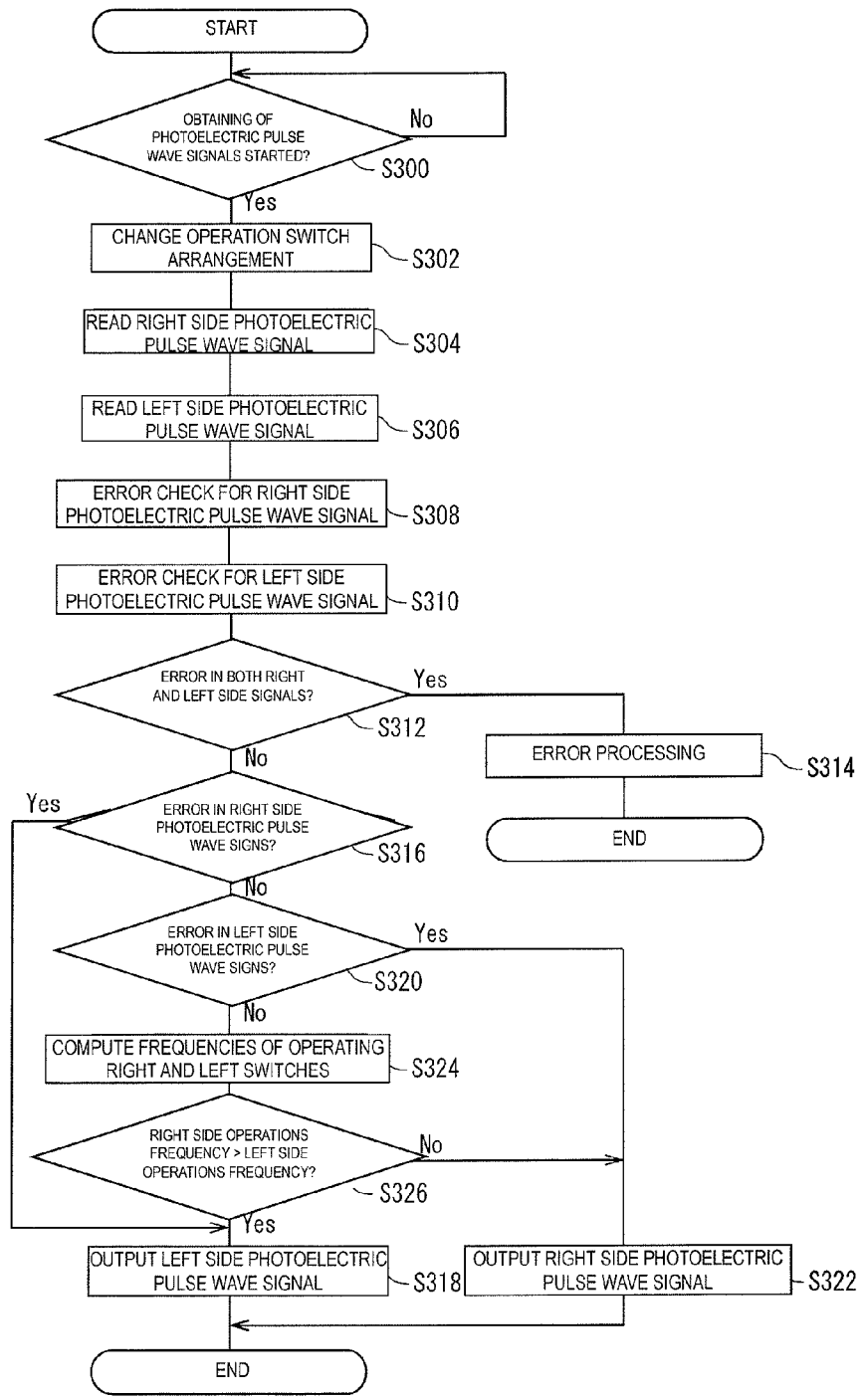
FIG. 9 is a flowchart illustrating the processing steps of biosignal selection processing performed by the mobile apparatus according to the third embodiment.

Referring to FIG. 9, the operation of the smart phone 3 will now be described. FIG. 9 is a flowchart illustrating the processing steps of biosignal selection processing performed by the smart phone 3. Note that this processing is performed at a predetermined timing in the signal processing unit 103.

In step S300, it is determined whether or not the fingertips of a user have touched the photoelectric pulse wave sensing units 41 and 42 and a process of obtaining a photoelectric pulse wave signal has been started. Here, when it is determined that the process of obtaining a photoelectric pulse wave signal has been started, the flow proceeds to step S302. On the hand, when it is determined that the process of obtaining a photoelectric pulse wave signal has not been started, the present step is repeated until the fingertips of a user touch the photoelectric pulse wave sensing units 41 and 42 and a process of obtaining a photoelectric pulse wave signal is started.

In step S302, the arrangement of the plurality of operation switches 31 and the plurality of operation switches 32 displayed on the touch screen 21 is changed. In more details, the arrangement the operation switches 31 displayed on the touch screen 21 is changed in such a manner that the operation switches 31 are arranged along the circular arc 510 of a virtual circle whose center is located at the carpometacarpal joint 500 of the thumb of the right hand 501 and whose radius is the distance from the carpometacarpal joint 500 to the tip of the thumb. Similarly, the arrangement the operation switches 32 displayed on the touch screen 21 is changed in such a manner that the operation switches 32 are arranged along the circular arc 512 of a virtual circle whose center is located at the carpometacarpal joint 503 of the thumb of the left hand 502 and whose radius is the distance from the carpometacarpal joint 503 to the tip of the thumb.

Then in step S304, a photoelectric pulse wave signal obtained from the photoelectric pulse wave sensing unit 42 with which the right hand 501 is in contact is read. Similarly, in step S306, a photoelectric pulse wave signal obtained from the photoelectric pulse wave sensing unit 41 with which the left hand 502 is in contact is read.

In step S308 which follows, an error check (for example, whether or not the voltage of the signal is within a predetermined range) is performed for the photoelectric pulse wave signal read from the photoelectric pulse wave sensing unit 42 with which the right hand 501 is in contact. Similarly, in step S310, an error check is performed for the photoelectric pulse wave signal read from the photoelectric pulse wave sensing unit 41 with which the left hand 502 is in contact.

Then in step S312, it is determined whether or not both of the photoelectric pulse wave signal read from the photoelectric pulse wave sensing unit 42 and the photoelectric pulse wave signal read from the photoelectric pulse wave sensing unit 41 are abnormal, as a result of error checking performed in steps S308 and S310. When it is determined that both the photoelectric pulse wave signals are abnormal (i.e., determined to have an error), the data (photoelectric pulse wave signal) is discarded in step S314, and then the present processing is temporarily stopped. On the other hand, when it is determined otherwise in step S312, that is, it is determined that both or either one of the photoelectric pulse wave signal read from the photoelectric pulse wave sensing unit 42 and the photoelectric pulse wave signal read from the photoelectric pulse wave sensing unit 41 is normal, the flow proceeds to step S316.

In step S316, it is determined whether or not the photoelectric pulse wave signal read from the photoelectric pulse wave sensing unit 42 is abnormal. Here, when it is determined that the photoelectric pulse wave signal is normal, the flow proceeds to step S320. On the other hand, when it is determined that the photoelectric pulse wave signal is abnormal, the photoelectric pulse wave signal read from the photoelectric pulse wave sensing unit 41 is selected and output in step S318. Then the present processing is temporarily stopped.

In step S320, it is determined whether or not the photoelectric pulse wave signal read from the photoelectric pulse wave sensing unit 41 is abnormal. Here, when it is determined that the photoelectric pulse wave signal is normal, the flow proceeds to step S324. On the other hand when it is determined that the photoelectric pulse wave signal is abnormal, the photoelectric pulse wave signal read from the photoelectric pulse wave sensing unit 42 is selected and output in step S322. Then the present processing is temporarily stopped.

In step S324, the respective numbers of output changes of the operation switches 31 operated by the right hand 501 and the operation switches 32 operated by the left hand 502 are counted, whereby respective operation frequencies are obtained.

Then in step S326, it is determined whether or not the operation frequency of the operation switches 31 operated by the right hand 501 is higher than the operation frequency of the operation switches 32 operated by the left hand 502. When it is determined that the operation frequency of the operation switches 31 is higher than the operation frequency of the operation switches 32, the flow proceeds to the above-described step S318, and in step S318, the photoelectric pulse wave signal read from the photoelectric pulse wave sensing unit 41 is selected and output. Then the present processing is temporarily stopped. On the other hand, when it is determined that operation frequency of the operation switches 32 is higher than the operation frequency of the operation switches 31, the flow proceeds to the above-described step S322, and in step S322, the photoelectric pulse wave signal read from the photoelectric pulse wave sensing unit 42 is selected and output. Then the present processing is temporarily stopped.

According to the present embodiment, when photoelectric pulse wave signals are obtained, for the right hand 501 and the left hand 502, the arrangement of the operation switches 31 and 32 are changed in such a manner that the operation switches 31 and 32 are respectively arranged along the circular arcs 510 and 512 of virtual circles whose centers are respectively located at the carpometacarpal joint 500 of the right hand 501 and a carpometacarpal joint 503 of the left hand 502 and whose radiuses are respectively the distances from the carpometacarpal joints 500 and 503 to the tips of the thumbs. Hence, during the operations performed by the thumbs, movements, together with the thumbs, of fingers other than the thumbs and the palms are suppressed. Hence, it is possible to decrease body movement noise generated by body movement at the time of operating the smart phone 3 with the thumbs. Further, in the present embodiment, a photoelectric pulse wave signal obtained from one of the right hand 501 and the left hand 502 which corresponds to a lower operation frequency is selected and output. Hence, it is possible to further decrease the influence of body movement noise generated by body movement at the time of operating the smart phone 3 with the thumbs.

Fourth Embodiment

Figure 10:
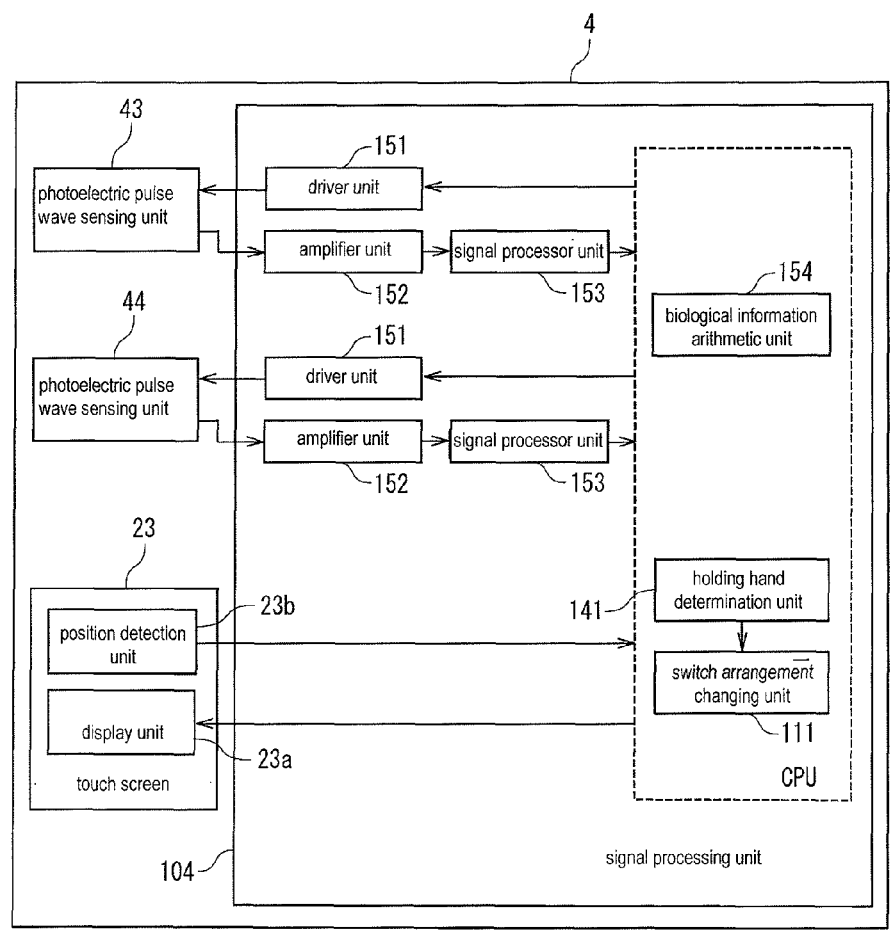
FIG. 10 is a block diagram illustrating the configuration of a mobile apparatus according to a fourth embodiment.
Figure 11:
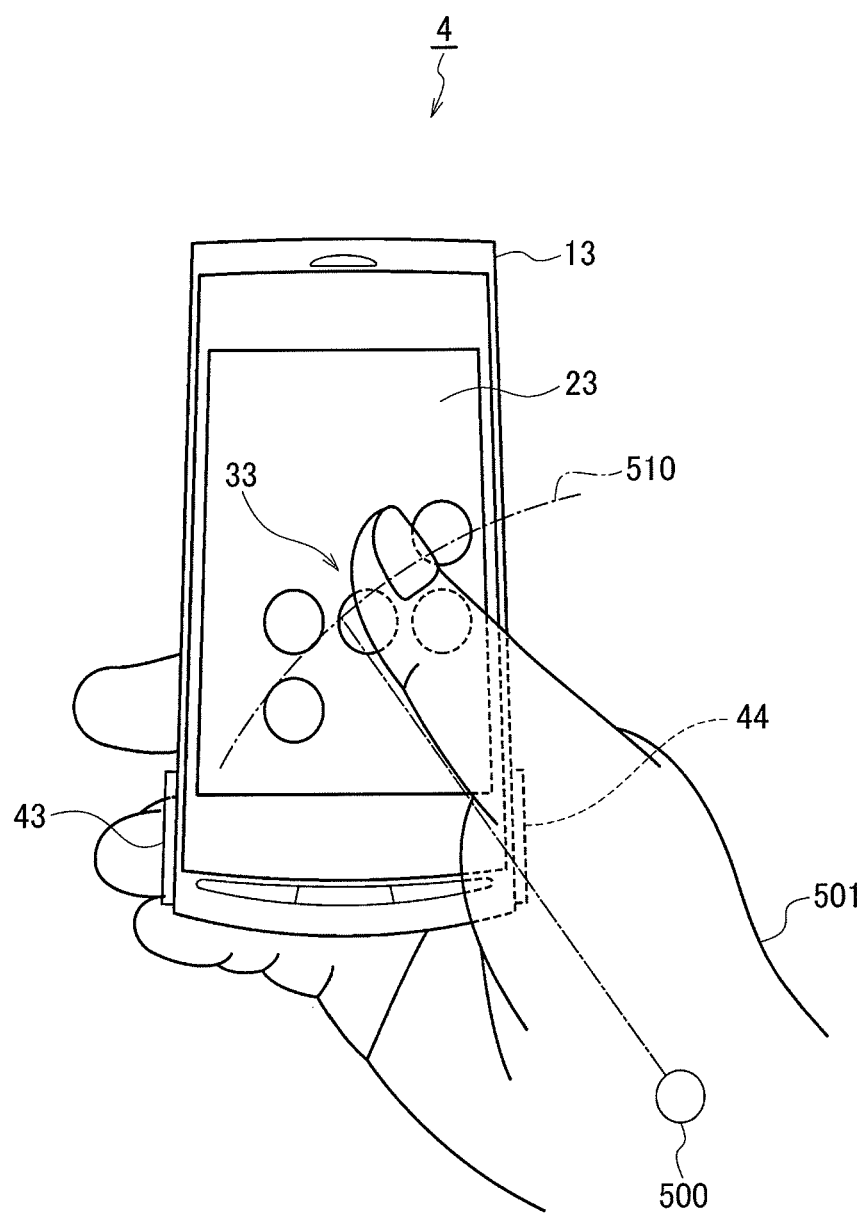
FIG. 11 is a diagram illustrating the arrangement of operation switches in the case where the mobile apparatus according to the fourth embodiment is held in a right hand.
Figure 12:
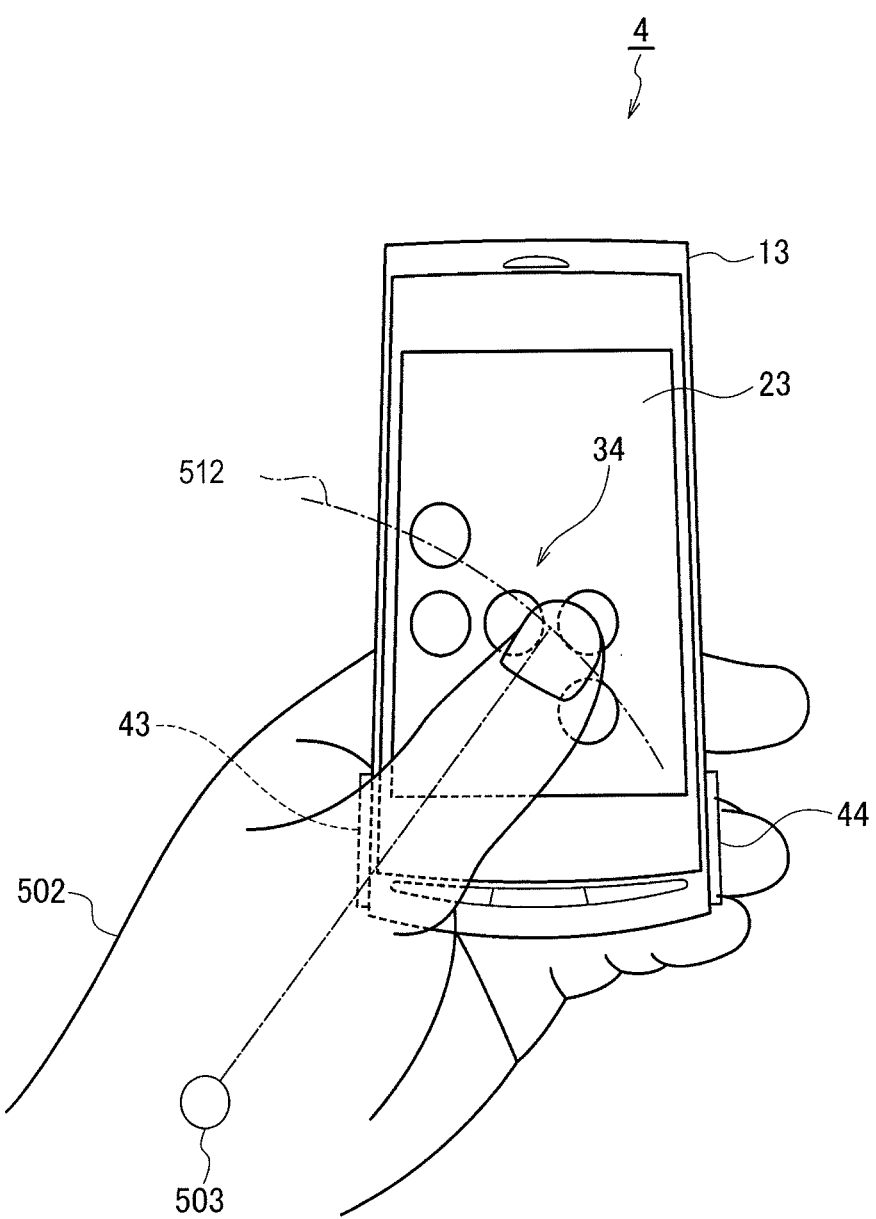
FIG. 12 is a diagram illustrating the arrangement of operation switches in the case where the mobile apparatus according to the fourth embodiment is held in a left hand.

Next, referring to FIG. 10 as well as FIG. 11, the configuration of a smart phone (mobile apparatus) 4 according to a fourth embodiment will be described. FIG. 10 is a block diagram illustrating the configuration of the smart phone 4. FIG. 11 is a diagram illustrating the arrangement of operation switches in the case where the smart phone 4 is held in the right hand 501, and FIG. 12 is a diagram illustrating the arrangement of operation switches in the case where the smart phone 4 is held in the left hand 502. Note that, in FIGS. 10, 11, and 12, components that are the same as or equivalent to those in the first embodiment are denoted by the same reference symbols.

A smart phone may be used while being held in a single hand. Compared with the smart phone 1 described above, the smart phone 4 has an additional function of determining which hand (right hand or left hand) of a user is holding the smart phone and changing the arrangement of a related plurality of switches 33 (34) displayed on a touch screen 23. For this purpose, the smart phone 4 includes a signal processing unit 104 instead of the signal processing unit 101 described above. Unlike the signal processing unit 101, the signal processing unit 104 further includes a holding hand determination unit 141 in addition to the configuration of the signal processing unit 101 described above. Note that in the present embodiment, the two photoelectric pulse wave sensing units 43 and 44 are attached to the lower end portions of the side surfaces of a main body 13, as illustrated in FIGS. 11 and 12. Since the rest of the configuration is the same as or similar to that of the smart phone 1, the description thereof is omitted here.

The holding hand determination unit 141 determines how the smart phone 4 is held, i.e., whether the smart phone 4 is held in both hands or in a single hand, and in the case of a single hand, whether the single hand is the right hand or the left hand, on the basis of a signal from the photoelectric pulse wave sensing unit 41 and a signal from the photoelectric pulse wave sensing unit 42. In other words, the holding hand determination unit 141 functions as the holding hand determination means.

More specifically, the holding hand determination unit 141 determines that the smart phone 4 is held in the two hands 501 and 502 when a normal signal (output) above a predetermined level is obtained from each of the photoelectric pulse wave sensing unit 43 and the photoelectric pulse wave sensing unit 44. The holding hand determination unit 141 determines that the smart phone 4 is held in the left hand 502 (single hand) when a normal signal (output) is obtained only from the photoelectric pulse wave sensing unit 43. On the other hand, the holding hand determination unit 141 determines that the smart phone 4 is held in the right hand 501 (single hand) when a normal signal (output) is obtained only from the photoelectric pulse wave sensing unit 44. Note that a configuration may be employed in which the holding hand is detected by attaching, to the main body 13 of the smart phone 3, a proximity switch or the like that can detect contact with a human body or a temperature sensor or the like that measures a body surface temperature, besides the photoelectric pulse wave sensing units 43 and 44. The detected information indicating the holding hand is output to the switch arrangement changing unit 111.

The switch arrangement changing unit 111, when it is determined that the smart phone 4 is held in the right hand 501, as illustrated in FIG. 11, changes the arrangement of the operation switches 33 in such a manner that the operation switches 33 are arranged along the circular arc 510 of a virtual circle whose center is located at the carpometacarpal joint 500 of the thumb of the right hand 501 holding the smart phone 4 and whose radius is the distance from the carpometacarpal joint 500 to the tip of the thumb.

On the other hand, when it is determined that the smart phone 4 is held in the left hand 502, as illustrated in FIG. 12, the switch arrangement changing unit 111 changes the arrangement of the operation switches 34 in such a manner that the operation switches 34 are arranged along the circular arc 512 of a virtual circle whose center is located at the carpometacarpal joint 503 of the thumb of the left hand 502 holding the smart phone 4 and whose radius is the distance from the carpometacarpal joint 503 to the tip of the thumb.

Figure 13:
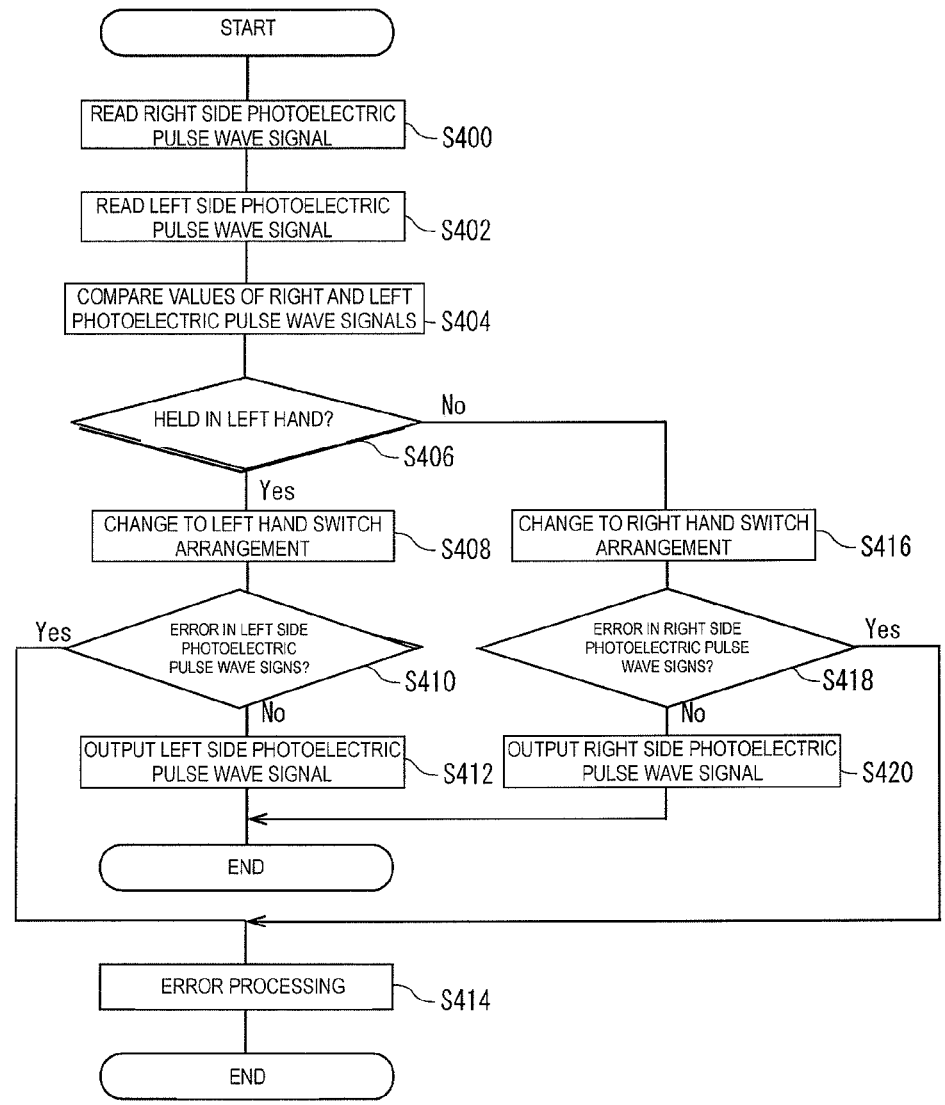
FIG. 13 is a flowchart illustrating the processing steps of biosignal measurement processing performed by the mobile apparatus according to the fourth embodiment.

Next, referring to FIG. 13, the operation of the smart phone 4 will be described. FIG. 13 is a flowchart illustrating the processing steps of biosignal measurement processing performed by the smart phone 4. Note that this processing is performed in the signal processing unit 104 at a predetermined timing.

In step S400, a photoelectric pulse wave signal obtained by the photoelectric pulse wave sensing unit 44 attached to the lower end portion of the right side surface of the main body 13 is read. Similarly, in step S402, a photoelectric pulse wave signal obtained by the photoelectric pulse wave sensing unit 43 attached to the lower end portion of the left side surface of the main body 13 is read.

Next, in step S404, the value of the photoelectric pulse wave signal, read in step S400, obtained from the photoelectric pulse wave sensing unit 44 is compared with the value of the photoelectric pulse wave signal, read in step S402, obtained from the photoelectric pulse wave sensing unit 43 are compared.

Then in step S406, on the basis of the comparison result in step S404, it is determined whether or not the smart phone 4 is held in the left hand 502 (whether or not the value of the photoelectric pulse wave signal obtained from the photoelectric pulse wave sensing unit 43 is larger (or the reflection amount is larger) than the value of the photoelectric pulse wave signal obtained from the photoelectric pulse wave sensing unit 44). Here, when it is determined that the smart phone 4 is held in the left hand 502, the flow proceeds to step S408. On the other hand, when it is determined that the smart phone 4 is not held in the left hand 502 (i.e., the smart phone 4 is held in the right hand 501), the flow proceeds to step S416.

In step S408, when it is determined that the smart phone 4 is held in the left hand 502, the arrangement of the operation switches 34 is changed in such a manner that the plurality of switches 34 are arranged along the circular arc 512 of a virtual circle whose center is located at the carpometacarpal joint 503 of the thumb of the left hand 502 and whose radius is the distance from the carpometacarpal joint 503 to the tip of the thumb (refer to FIG. 12).

Then in step S410, it is determined whether or not the photoelectric pulse wave signal read from the photoelectric pulse wave sensing unit 43 is abnormal. Here, when it is determined that the photoelectric pulse wave signal is normal, the photoelectric pulse wave signal is output in step S412, and the present processing is temporarily stopped. On the other hand, when it is determined that the photoelectric pulse wave signal is abnormal, after error determination has been made in step S414, the present processing is temporarily stopped.

On the other hand, when it is determined that the smart phone 4 is held in the right hand 501, in step S416, the arrangement of the operation switches 33 is changed in such a manner that the plurality of switches 33 are arranged along the circular arc 510 of a virtual circle whose center is located at the carpometacarpal joint 500 of the thumb of the right hand 501 and whose radius is the distance from the carpometacarpal joint 500 to the tip of the thumb (refer to FIG. 11).

Then in step S418, it is determined whether or not the photoelectric pulse wave signal read from the photoelectric pulse wave sensing unit 44 is abnormal. Here, when it is determined that the photoelectric pulse wave signal is normal, after the photoelectric pulse wave signal has been output in step S420, the present processing is temporarily stopped. On the other hand, when it is determined that the photoelectric pulse wave signal is abnormal, after error determination has been made in step S414 described above, the present processing is temporarily stopped.

According to the present embodiment, the arrangement of the operation switches 33 (34) are changed in such a manner that the operation switches 33 (34) are arranged along the circular arc 510 (512) of a virtual circle whose center is located at the carpometacarpal joint 500 (503) of the thumb of the hand 501 (502) holding the smart phone and whose radius is the distance from the carpometacarpal joint 500 (503) to the tip of the thumb. Hence, even in the case where the smart phone 4 is operated while being held in a single hand, during the operation performed by the thumb, movements, together with the thumb, of fingers other than the thumb and the palm are suppressed. Hence, it is possible to decrease body movement noise generated by body movement at the time of operating the smart phone 4 with the thumb.

Although the embodiments of the present invention have been described above, the present invention is not limited to the above embodiments and various modifications are possible. For example, although the above embodiments employ a configuration in which the plurality of operation switches 31, 32, 33, and 34 are displayed on the touch screens 21 and 23, a configuration may be employed in which hardware switches which can be arranged in an arrangement which can be changed are used. Further, the respective shapes and numbers of the operation switches, 31, 32, 33, and 34 are not limited to those in the above-described embodiments.

Note that when hardware switches are used, the operation switches 31 or the operation switches 32 may be arranged in a fixed manner along a circular arc of a virtual circle whose center is located at the carpometacarpal joint of a thumb and whose radius is the distance from the carpometacarpal joint to the tip of the thumb, rather than employing a configuration in which the arrangement of the operation switches is variable.

Although, in the first embodiment described above, the switch arrangement for a hand (the right hand 501 in the example of FIG. 2) performing operations is changed, a configuration may be employed in which through a prior setting that makes a photoelectric pulse wave signal be obtained from one of the two hands, for example, through a setting in which only the photoelectric pulse wave sensing unit 41 is attached or a photoelectric pulse wave signal is obtained preferentially from the photoelectric pulse wave sensing unit 41, the arrangement of the operation switches 31 displayed on the touch screen 21 is changed in such a manner that the operation switches 31 are arranged along the circular arc 510 of a virtual circle whose center is located at the carpometacarpal joint 500 of the thumb of a hand (the right hand 501 in this case) from which a photoelectric pulse wave signal is not being obtained and whose radius is the distance from the carpometacarpal joint 500 to the tip of the thumb. Note that instead of this configuration, a configuration may be employed in which a photoelectric pulse wave signal is obtained from the photoelectric pulse wave sensing unit 42 and the arrangement of the left hand 502 side operation switches is changed.

A configuration may be employed in which the operation switches are arranged or displayed, but an operation performed by a hand (the left hand 502 in the example of FIG. 2) from which a photoelectric pulse wave signal is being obtained is not accepted. Further, a configuration may be employed in which the operation switches for accepting an operation performed by a hand (the left hand 502 in the example of FIG. 2) from which a photoelectric pulse wave signal is being obtained are not displayed (arranged) (refer to FIG. 2).

In the third embodiment described above, when photoelectric pulse wave signals are obtained by the photoelectric pulse wave sensing units 41 and 42, for the right hand 501 and the left hand 502, the arrangement of the operation switches 31 and 32 is changed in such a manner that the operation switches 31 and 32 are respectively arranged along the circular arcs 510 and 512 of virtual circles whose centers are respectively the carpometacarpal joints 500 and 503 of the right hand 501 and the left hand 502 and whose radiuses are respectively the distances from the carpometacarpal joints 500 and 503 to the tips of the thumbs. However, the arrangement of the operation switches 31 and 32 need not necessarily be changed as described above. In other words, a configuration may be employed in which a biosignal is selected in accordance with the operation frequencies, while maintaining the normal arrangement of the operation switches 31 and 32.

REFERENCE SIGNS LIST 1, 2, 3, 4 smart phones (mobile apparatuses)
11, 13 main bodies
21, 23 touch screens
21a, 23a display units
21b, 23b position detection units
31, 32, 33, 34 operation switches
41, 42, 43, 44 photoelectric pulse wave sensing units (biosensors)
101, 102, 103, 104 signal processing units
111, 122 switch arrangement changing units
121 arrangement region setting unit
131 operation frequency obtaining unit
132 biosignal selection unit
141 holding hand determination unit
500, 503 carpometacarpal joints

The invention claimed is:

1. A mobile apparatus comprising:
   a main body;
   a touch screen disposed on a front surface of the main body and configured to display at least one operation switch at a display position for receiving an input signal from at least one digit of a hand of a user holding the mobile apparatus, wherein the at least one digit is a thumb of the hand; and
   a biosensor disposed on a top side surface of the main body that is above the front surface and extends in a direction orthogonal to the front surface, the biosensor being configured to detect a biosignal from another digit of the hand of the user holding the mobile apparatus, other than the at least one digit of the hand, or of another hand of the user holding the mobile apparatus,
   wherein, in response to detecting the biosignal, the at least one operation switch is displayed at the display position on the touch screen arranged along a circular arc of a virtual circle having a center point located near a carpometacarpal joint of the at least one digit of the hand of the user holding the mobile apparatus and having a radius that corresponds to a distance from the carpometacarpal joint to a tip of the at least one digit of the hand of the user holding the mobile apparatus, wherein the center point and the radius are set in advance based on stochastic data, and
   wherein the biosensor is a photoelectric pulse wave sensor, and the detected biosignal is a photoelectric pulse wave signal, wherein the at least one operation switch is displayed at the display position on the touch screen in response to the another digit of the hand holding the mobile apparatus, other than the at least one digit of the hand, or of the another hand of the user holding the mobile apparatus touching the photoelectric pulse wave sensor.

2. The mobile apparatus according to claim 1, wherein the touch screen displays a plurality of operations switches at a plurality of displays positions arranged along the circular arc.

3. The mobile apparatus according to claim 1, wherein the least one operation switch does not accept an input signal from the another digit from which the biosignal is detected by the biosensor.

4. The mobile apparatus according to claim 1, further comprising a switch arrangement unit configured to change the display position for the at least one operation switch such that the at least one operation switch is displayed at the display position for receiving the input signal from the at least one digit of the hand of a user holding the mobile apparatus when the biosignal is being detected by the biosensor from the another digit of the another hand of the user holding the mobile apparatus.

5. The mobile apparatus according to claim 4, wherein the touch screen displays a plurality of operations switches at a plurality of displays positions arranged along the circular arc.

6. The mobile apparatus according to claim 1, further comprising a holding hand determination unit, wherein the at least one operation switch is displayed on the touch screen at the display position based on whether the holding hand determination unit determines that the hand is a right hand or a left hand of the user.

7. The mobile apparatus according to claim 1, further comprising:
   a position information obtaining unit configured to obtain position information of a region on the touch screen touched by the at least one digit of the hand of a user holding the mobile apparatus; and
   a position region setting unit configured to set a target region on the basis of the obtained position information,
   wherein the at least one operation switch is displayed at the display position that overlaps with the target region.

8. The mobile apparatus according to claim 1, wherein when a voltage of the photoelectric pulse wave signal is outside a predetermined voltage range, data relating to the detected biosignal is discarded.

9. The mobile apparatus according to claim 1, further comprising a signal processing unit configured to obtain biological information from the detected biosignal and store the biological information in electronic memory.

10. The mobile apparatus according to claim 9, wherein the biological information is a pulse rate of the user.

11. A mobile apparatus comprising:
    a main body;
    a touch screen disposed on a front surface of the main body and configured to display a plurality of operation switches at a plurality of respective display positions for receiving input signals from respective digits of a left hand and a right hand of a user holding the mobile apparatus, wherein the respective digits are a thumb of the left hand and a thumb of the right hand;
    a plurality of biosensors disposed on at least a top side surface of the main body that is above the front surface and extends in a direction orthogonal to the front surface, the plurality of biosensors being configured to detect biosignals respectively from another digit of the left hand of the user holding the mobile apparatus and another digit of the right hand of the user holding the mobile apparatus other than the respective digits of the left hand and the right hand of the user holding the mobile apparatus; and
a biosignal selection unit configured to selectively output biosignals detected by the respective biosensors,
wherein, in response to detecting the respective biosignals, the plurality of operation switches are displayed at the respective display positions on the touch screen and are arranged along circular arcs of a pair of virtual circles having respective center points located near carpometacarpal joints of the respective digits of the left hand and the right hand of the user holding the mobile apparatus and radiuses that correspond to a distance from the respective carpometacarpal joint of the respective digits of the left hand and the right hand to a tip of the respective digits of the left hand and the right hand of the user holding the mobile apparatus, wherein the center points and the radiuses are set in advance based on stochastic data, and
wherein the plurality of biosensors are each photoelectric pulse wave sensors, and the detected biosignals are photoelectric pulse wave signals, wherein the plurality of operation switches are displayed at the respective display positions on the touch screen in response to the respective another digit of the left hand of the user holding the mobile apparatus and the respective another digit of the right hand of the user holding the mobile apparatus, other than the respective digits of the left hand and the right hand of the of the user holding the mobile apparatus, touching the respective photoelectric pulse wave sensor.

12. The mobile apparatus according to claim 11, further comprising a switch arrangement changing unit configured to change the respective display positions of the plurality of operation switches respectively for the left hand and the right hand.

13. The mobile apparatus according to claim 11, further comprising an operation frequency obtaining unit configured to obtain operation frequencies of respective input signals from the left hand and the right hand,
wherein the biosignal selection unit preferentially selects and outputs a biosignal obtained from one of the left hand and the right hand, whose operation frequency is lower.

14. The mobile apparatus according to claim 11, further comprising a holding hand determination unit, wherein at least one operation switch of the plurality of operation switches is displayed on the touch screen at the respective display position based on whether the holding hand determination unit determines that a hand is a left or a right hand of the user.

15. The mobile apparatus according to claim 11, further comprising:
a position information unit configured to obtain position information of a region on the touch screen touched by the respective digits of the right and left hands; and
a position region setting unit configured to set a target region on the basis of the obtained position information,
wherein the at least one of the plurality of operation switches is displayed at the respective display position that overlaps the region.

* * * * *